US009618550B2

(12) United States Patent
Nakamura et al.

(10) Patent No.: US 9,618,550 B2
(45) Date of Patent: Apr. 11, 2017

(54) APPARATUS FOR FREQUENCY ANALYZING A MEASUREMENT TARGET AND METHOD OF FREQUENCY ANALYZING A MEASUREMENT TARGET

(71) Applicant: HAMAMATSU PHOTONICS K.K., Hamamatsu-shi, Shizuoka (JP)

(72) Inventors: Tomonori Nakamura, Hamamatsu (JP); Akihiro Otaka, Hamamatsu (JP); Mitsunori Nishizawa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 330 days.

(21) Appl. No.: 14/535,709

(22) Filed: Nov. 7, 2014

(65) Prior Publication Data

US 2015/0130474 A1 May 14, 2015

(30) Foreign Application Priority Data

Nov. 12, 2013 (JP) ................. 2013-233776

(51) Int. Cl.
*G01R 23/17* (2006.01)
*G01R 31/311* (2006.01)
*G01N 21/95* (2006.01)

(52) U.S. Cl.
CPC ......... *G01R 23/17* (2013.01); *G01N 21/9501* (2013.01); *G01N 2201/06113* (2013.01); *G01N 2201/08* (2013.01); *G01R 31/311* (2013.01)

(58) Field of Classification Search
CPC .. G01R 31/2851; G01R 31/311; G01N 21/55; G01N 21/88; G01N 21/9501; G01N 2201/06113; G01N 2201/08; H01L 22/12
(Continued)

(56) References Cited

U.S. PATENT DOCUMENTS 5,767,688 A * 6/1998 Takahashi ............. G01R 1/071
324/754.23
6,381,157 B2 * 4/2002 Jensen ................ H02M 3/1584
363/65
(Continued)

FOREIGN PATENT DOCUMENTS

JP 2007-064975 A 3/2007
JP 2010-271307 A 12/2010
(Continued)

*Primary Examiner* — Hoai-An D Nguyen
(74) *Attorney, Agent, or Firm* — Drinker Biddle & Reath LLP

(57) ABSTRACT

A semiconductor device testing apparatus 1A includes a tester unit 16 that generates an operational pulse signal, an optical sensor 10 that outputs a detection signal as a response to the operational pulse signal, a pulse generator 17 that generates a reference signal containing a plurality of harmonics for the operational pulse signal in synchronization with the operational pulse signal, a spectrum analyzer 13 that receives the detection signal and acquires a phase and amplitude of the detection signal at a detection frequency, a spectrum analyzer 14 that receives the reference signal and acquires a phase of the reference signal at a detection frequency, and an analysis control unit 18 that acquires a time waveform of the detection signal based on the phase and the amplitude of the detection signal acquired by the spectrum analyzer 13 and the phase of the reference signal acquired by the spectrum analyzer 14.

18 Claims, 8 Drawing Sheets

(58) Field of Classification Search
USPC ....... 324/500, 501, 520, 76.11, 76.12, 76.19, 324/76.39, 76.41, 76.56, 76.69
See application file for complete search history.

(56) References Cited

U.S. PATENT DOCUMENTS

| | | | |
|---|---|---|---|
| 8,384,372 B1 * | 2/2013 | Behlow, Jr. ........... | G01N 29/036 324/76.41 |
| 2012/0307249 A1 | 12/2012 | Nakamura et al. | |
| 2015/0129768 A1 * | 5/2015 | Koizumi ............ | G01N 21/3581 250/341.1 |

FOREIGN PATENT DOCUMENTS

| | | |
|---|---|---|
| JP | 2014-092514 A | 5/2014 |
| WO | WO-2007/136681 A2 | 11/2007 |

* cited by examiner

APPARATUS FOR FREQUENCY ANALYZING A MEASUREMENT TARGET AND METHOD OF FREQUENCY ANALYZING A MEASUREMENT TARGET

BACKGROUND OF THE INVENTION

Field of the Invention

The present invention relates to a frequency analysis apparatus and a frequency analysis method.

Related Background Art

A light probing technology referred to as EOP (Electro Optical Probing) or EOFM (Electro-Optical Frequency Mapping) is known as a technology for testing an integrated circuit. In the light probing technology, an integrated circuit is irradiated with light emitted from a light source, reflected light reflected by the integrated circuit is detected by an optical sensor, and a detection signal is acquired. Also, a desired frequency in the acquired detection signal is selected and amplitude energy thereof is displayed over time or displayed in two-dimensional mapping. Accordingly, a location of a circuit operating at the desired frequency can be identified.

Patent Document 1: Japanese Unexamined Patent Application Publication No. 2007-64975

Patent Document 2: Japanese Unexamined Patent Application Publication No. 2010-271307

The light probing technology as described above is a very effective technology since a fault location or a failure cause in a semiconductor device such as an integrated circuit can be identified. Here, in a technology for performing measurement of a predetermined frequency, such as a light probing technology, measuring a detection signal at a high band frequency is desired.

Therefore, an object of the present invention is to provide a frequency analysis apparatus and a frequency analysis method capable of measuring a detection signal at a high band frequency.

SUMMARY OF THE INVENTION

An apparatus for frequency analyzing a measurement target of the present invention includes: an operational pulse signal generator configured to generate an operational pulse signal to be input to the measurement target; a detector configured to output a detection signal as a response to the operational pulse signal; a reference signal generator configured to generate a reference signal containing a plurality of harmonics for the operational pulse signal in synchronization with the operational pulse signal; a first electronic device configured to receive the detection signal output by the detection unit and acquire a phase and amplitude of the detection signal at a detection frequency; a second electronic device configured to receive the reference signal generated by the reference signal generation unit and acquire a phase of the reference signal at the detection frequency; and an analysis system configured to acquire a time waveform of the detection signal based on the phase and the amplitude of the detection signal acquired by the first electronic device and the phase of the reference signal acquired by the second electronic device.

In this apparatus, the reference signal generator generates the reference signal containing the plurality of harmonics for the operational pulse signal to be input to the measurement target in synchronization with the operational pulse signal. Also, the phase and the amplitude of the detection signal at the detection frequency are acquired in the first electronic device, and the phase of the reference signal at the same detection frequency is acquired in the second electronic device. Since a plurality of harmonics are contained in the reference signal, it is possible to obtain the phase difference between the detection signal and the reference signal in the high band, and the amplitude of the detection signal in the high band by using the detection frequency that is a frequency in the high band. Thus, according to this apparatus, it is possible to measure the detection signal at the high band frequency.

Further, the apparatus of the present invention may further include a light source configured to generate light; and an optical system configured to irradiate the measurement target with the light, and guide reflected light of the light, wherein the detector may be an optical sensor configured to output the detection signal by detecting the reflected light. In this configuration, since the detection signal is acquired by the detector which is an optical sensor detecting the reflected light, the acquisition of the detection signal as a response to the operational pulse signal is performed easily and reliably. Thus, the measurement of the detection signal in the high band can be simplified and measurement precision can be increased.

Further, the apparatus of the present invention may further include a changing device configured to change the detection frequency in synchronization with the reference signal. According to this configuration, it is possible to perform the measurement of the detection signal in a plurality of bands reliably and with high precision.

Further, the apparatus of the present invention may further include a switching device configured to perform switching so that the detection signal or the reference signal is input to the first electronic device. According to this configuration, the input to the first electronic device can be the reference signal in place of the detection signal. Therefore, it is possible to input the reference signal to both of the first electronic device and the second electronic device, as necessary.

Further, in the apparatus of the present invention, the switching device may perform switching so that the reference signal is input to the first electronic device, the first electronic device may acquire the phase of the reference signal at the detection frequency, and the analysis system may acquire a phase error between the first electronic device and the second electronic device based on the phases of the reference signals acquired by the first electronic device and the second electronic device. Since the phase error between the first electronic device and the second electronic device is acquired, it is possible to measure the detection signal in consideration of the phase error between the first electronic device and the second electronic device when the detection signal is input to the first electronic device. The measurement precision of the detection signal in the high band is further improved.

Further, in the apparatus of the present invention, the reference signal generator may generate the reference signal containing harmonics from a fundamental harmonic to at least a tenth harmonic for the operational pulse signal. It is possible to measure the detection signal at a high band frequency by using the detection frequency that is a frequency in a high band such as the tenth harmonic.

Further, in the apparatus of the present invention, the reference signal generator may be a pulse generator, and may generate, as the reference signal, a pulse signal having a shorter pulse width than a repetition period of the operational pulse signal. According to this configuration, it is possible to change the detection frequency in a period between pulses of the operational pulse signal. Accordingly, it is possible to perform the measurement of the detection signal in a plurality of bands reliably and with high precision.

Further, in the apparatus of the present invention, the reference signal generator may continuously generate a signal at a different frequency as the reference signal. According to this configuration, for example, it is possible to change the detection frequency in a period when a frequency of a sine wave of the reference signal changes. Accordingly, it is possible to perform the measurement of the detection signal in a plurality of high bands reliably and with high precision.

Further, in the apparatus of the present invention, the first electronic device and the second electronic device may be one or more spectrum analyzers. It is possible to reliably acquire the phase or the like by using the spectrum analyzer.

A method of frequency analyzing a measurement target of the present invention includes: generating an operational pulse signal to be input to the measurement target; outputting a detection signal as a response to the operational pulse signal; generating a reference signal containing a plurality of harmonics for the operational pulse signal in synchronization with the operational pulse signal; by a first electronic device, acquiring a phase and amplitude of the detection signal at a detection frequency based on the detection signal; by a second electronic device, acquiring a phase of the reference signal at a detection frequency based on the reference signal; and acquiring a time waveform of the detection signal based on the phase and the amplitude of the detection signal and the phase of the reference signal.

DESCRIPTION OF THE PREFERRED EMBODIMENTS

Hereinafter, preferred embodiments of the present invention will be described in detail with reference to the drawings. Further, the same portions are denoted with the same reference signs throughout the drawings and repeated description is omitted.

[First Embodiment]

Figure 1:
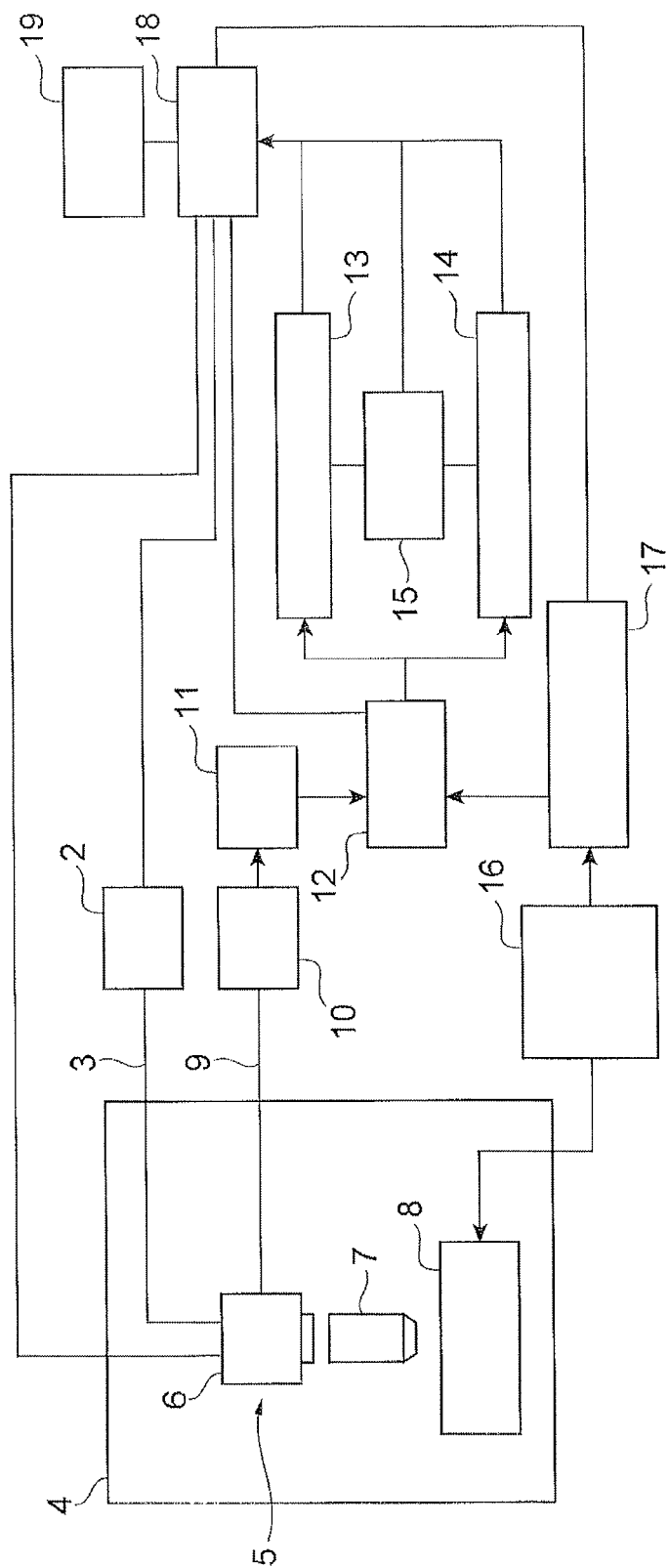
FIG. 1 is a diagram illustrating a configuration of a semiconductor device testing apparatus of a first embodiment of the present invention.

A semiconductor device testing apparatus 1A according to a first embodiment is an apparatus for testing a semiconductor device 8 that is a device under test (DUT), such as identifying a location in which an abnormality occurs in the semiconductor device 8, as illustrated in. FIG. 1. Specifically, the semiconductor device testing apparatus 1A is a frequency analysis apparatus that performs frequency analysis of a response to an operational signal of the semiconductor device 8, which is a measurement target.

The semiconductor device 8 includes, for example, an integrated circuit having a PN junction of a transistor or the like (for example, small scale integration (SSI), medium scale integration (MSI), large scale integration (LSI), very large scale integration (VLSI), ultra large scale integration (ULSI), or giga scale integration (GSI)), or a MOS transistor and a bipolar transistor for a high current and a high voltage. Further, the semiconductor device 8 may be a semiconductor device in which modulation by heat is applied to a substrate.

The semiconductor device 8 is driven with a predetermined operational pulse signal input by a tester unit 16. Therefore, testing in a desired operating state of the semiconductor device 8 can be performed by inputting an operational pulse signal (test pattern) corresponding to driving desired to be tested to the semiconductor device 8. The tester unit 16 is an operational pulse signal generation unit that generates the operational pulse signal that is input to the semiconductor device 8. Specifically, the tester unit 16 includes a pulse generator that generates the operational pulse signal for operating the semiconductor device 8, a tester that inputs the operational pulse signal to the semiconductor device 8, and a power supply. The operational pulse signal (test pattern) is generated based on a reference clock of the pulse generator of the tester unit 16. Further, the tester unit 16 inputs information on the operational pulse signal (for example, the operational pulse signal, a fundamental frequency or a fundamental period of the operational pulse signal, a reference clock of the pulse generator of the tester unit 16, or a frequency or a period of the reference clock) to the pulse generator 17 at the same time as input to the semiconductor device 8.

The semiconductor device testing apparatus 1A includes a laser light source 2. The laser light source 2 is a light generation unit that generates irradiation light that is coherent light (laser light) with which the semiconductor device 8 is irradiated. The light emitted from the laser light source 2 is guided to a scan optical system (optical system) 5 via a polarization preserving single-mode optical fiber 3 for probe light. The scan optical system 5 includes a scan head 6 and a lens system 7. Accordingly, a predetermined location of the semiconductor device 8 is irradiated with the light guided to the scan optical system 5, and the semiconductor device 8 is scanned two-dimensionally in a region irradiated with the light. Further, the scan optical system 5 guides reflected light of the irradiation light radiated to the semiconductor device 8. The reflected light is guided to an optical sensor (light detection unit) 10 via an optical fiber 9 for return light. Further, the scan optical system 5 and the semiconductor device 8 are arranged within a dark box 4.

The optical sensor 10 detects the reflected light guided by the scan optical system 5 and outputs a detection signal. The optical sensor 10 is, for example, an avalanche photodiode or a photodiode. Since this reflected light is modulated according to the operational pulse signal input to the semiconductor device 8, the optical sensor 10 detects a signal from the semiconductor device 8 operating based on the operational pulse signal, and can output the detection signal as a response to the operational pulse signal input to the semiconductor device 8. The detection signal is input to the amplifier 11. The amplifier 11 amplifies the detection signal from the optical sensor 10 and inputs the detection signal after the amplification to a signal switching switch (switching unit) 12.

The pulse generator 17 is a reference signal generation unit that generates the reference signal containing a plurality of harmonics for the operational pulse signal based on the information on the operational pulse signal input by the tester unit 16. Here, the harmonics include a fundamental harmonic (primary harmonic) for the operational pulse signal, and an $n^{th}$ harmonic for the operational pulse signal (n is a positive integer) indicates a signal having a frequency of n times the frequency of the operational pulse signal (which is synonymous with a signal having a period of 1/n times the period of the operational pulse signal). The reference signal is a pulse signal having a shorter pulse width than the operational pulse signal (see FIG. 2). The plurality of harmonics for the operational pulse signal included in the reference signal have the same power. The pulse generator 17 generates the reference signal in synchronization with the operational pulse signal having a period of T (see FIG. 2), and inputs the reference signal to the signal switching switch 12. A device which generates a pulse signal, such as a pulse generator or a comb generator, for example, may be used as the pulse generator 17.

The pulse generator 17 generates the reference signal as follows. For example, when there is a signal having a duty ratio of 50 synchronized to the operational pulse signal, the signal is branched in two and one signal is input to and inverted by a NOT circuit. Also, the inverted signal and a non-inverted signal are input to an AND gate with a time lag of tens of ps. Then, a pulse signal having a width of tens of ps synchronized to the operational pulse signal is obtained from the AND gate. The pulse generator 17 outputs this pulse signal as the reference signal. Further, it is necessary for a pulse width of the reference signal to be shorter than a period of a harmonic corresponding to an upper limit of a period of a desired frequency. More specifically, when the detection frequency up to an $n^{th}$ harmonic is desired to be obtained, a pulse signal having a pulse width of less than 1/2n times the repetition period of the operational pulse signal (n is a positive integer) may be used as the reference signal. That is, for example, when the detection frequency up to a $100^{th}$ harmonic is desired to be obtained, a pulse signal having a pulse width of less than 1/200 times of the operational pulse signal may be used as the reference signal. When a pulse signal having a pulse width of less than 1/2n times the repetition period (fundamental period) of the operational pulse signal is used as the reference signal, a signal containing harmonics from a primary harmonic (fundamental harmonic) to an $n^{th}$ harmonic for the operational pulse signal can be used as the reference signal. The reference signal contains harmonics from a primary harmonic (fundamental harmonic) to at least a tenth harmonic for the operational pulse signal, and may preferably be a signal containing harmonics from the primary harmonic to a $100^{th}$ harmonic. In the case of a signal containing harmonics from a primary harmonic (fundamental harmonic) to at least a tenth harmonic for the operational pulse signal (that is, n=10), a pulse signal having a pulse width of less than 1/20 times the repetition period (fundamental period) of the operational pulse signal may be output as the reference signal.

The signal switching switch 12 inputs the detection signal or the reference signal to the spectrum analyzer (first electrical measurement unit) 13 or the spectrum analyzer (second electrical measurement unit) 14. Specifically, the signal switching switch 12 switches and inputs the detection signal or the reference signal to be input to the spectrum analyzer 13. Further, the signal switching switch 12 inputs the reference signal to the spectrum analyzer 14.

The spectrum analyzer (a first spectrum analyzer) 13 receives any one of the detection signal and the reference signal, and acquires a phase and amplitude of an input signal at the detection frequency. The spectrum analyzer 13 inputs the acquired phase and amplitude to the analysis control unit 18. Further, the spectrum analyzer 14 (a second spectrum analyzer) receives the reference signal, and acquires a phase of the reference signal at the detection frequency. The spectrum analyzer 14 inputs the acquired phase to the analysis control unit 18. Further, the spectrum analyzer 14 may also acquire the amplitude of the reference signal.

Here, the detection frequency is a frequency used to acquire, for example, the phase of the input signal in the spectrum analyzers 13 and 14. Each of the spectrum analyzers 13 and 14 includes a synthesizer, and is controlled so that a frequency of the synthesizer becomes the detection frequency. The spectrum analyzers 13 and 14 are electrically connected to each other via a signal synchronization unit 15.

The signal synchronization unit 15 synchronizes the spectrum analyzer 13 with the spectrum analyzer 14. Specifically, the signal synchronization unit 15 synchronizes a frequency and a phase of a base signal (time-based signal) for operating the spectrum analyzers 13 and 14. Accordingly, the spectrum analyzers 13 and 14 can acquire, for example, the phase of the input signal at the same detection frequency. The signal synchronization unit 15 is, for example, a means for outputting the time-based signal, and synchronizes the spectrum analyzers 13 and 14 by inputting the time-based signal to the spectrum analyzers 13 and 14. Further, the signal synchronization unit 15 may not necessarily be used as the means for synchronizing the spectrum analyzers 13 and 14, and the synchronization may be achieved, for example, by inputting the signal of one of the spectrum analyzers to the other spectrum analyzer. Further, the spectrum analyzers 13 and 14 and the signal synchronization unit 15 may be integrally configured.

Figure 2:
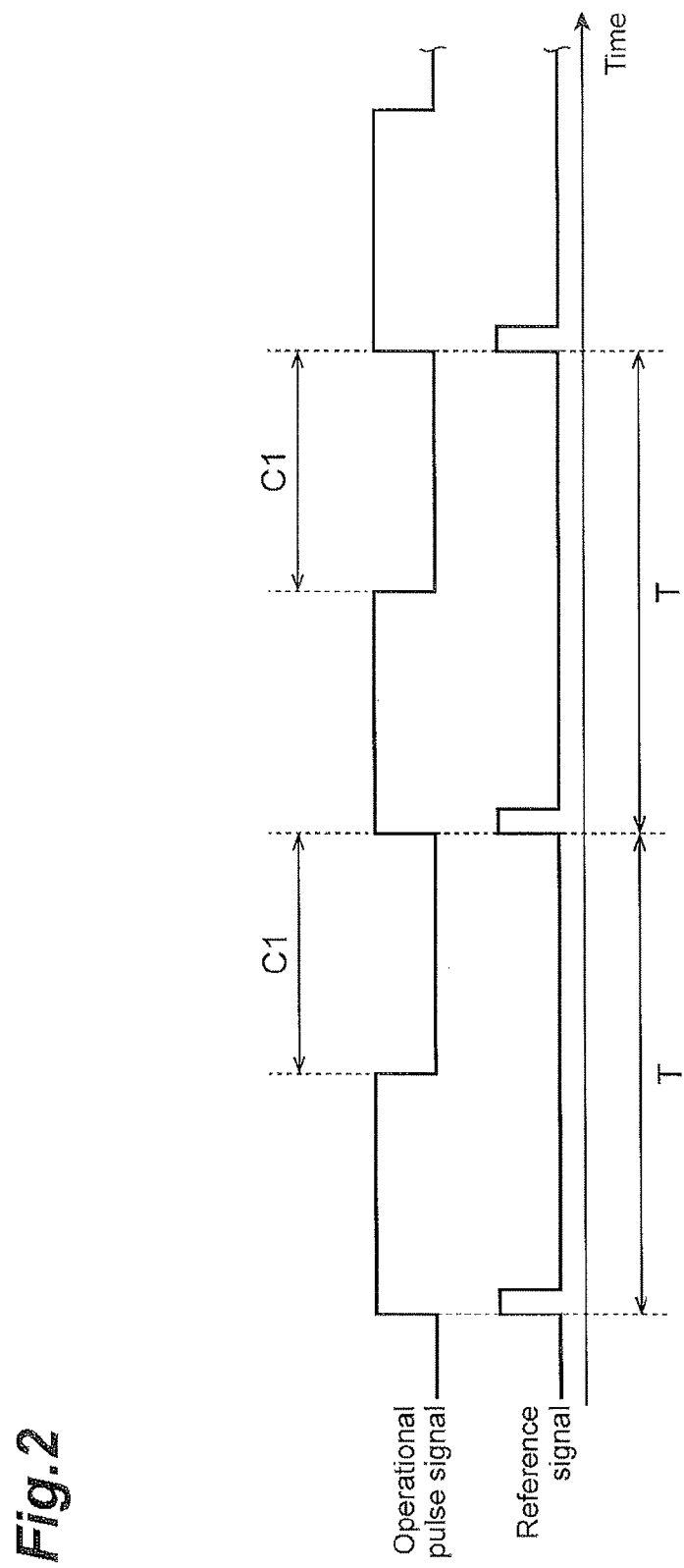
FIG. 2 is a graph illustrating an example of an operational pulse signal and a reference signal in the semiconductor device testing apparatus of FIG. 1.

Further, the signal synchronization unit 15 synchronizes the spectrum analyzers 13 and 14 with the pulse generator of the tester unit 16 (or the pulse generator 17). Accordingly, the operational pulse signal generated from the pulse generator of the tester unit 16 and the reference signal generated from the pulse generator 17 are synchronized, so that the detection frequencies of the spectrum analyzers 13 and 14 can be changed (changing unit). Specifically, the signal synchronization unit 15 synchronizes the spectrum analyzers 13 and 14 with the pulse generator of the tester unit 16 (or the pulse generator 17), such that, for example, the detection frequencies of the spectrum analyzers 13 and 14 can be changed in C1 between the pulses of the operational pulse signal, as illustrated in FIG. 2.

The analysis control unit 18 is an analysis unit that performs predetermined analysis based on information such as the phase input from the spectrum analyzers 13 and 14 at a plurality of detection frequencies. Specifically, the analysis control unit 18 acquires a time waveform of the detection signal (a response of the semiconductor device 8 to the operational pulse signal) using an inverse discrete Fourier transform based on the phase and the amplitude of the detection signal input from the spectrum analyzer 13 and the phase of the reference signal input from the spectrum analyzer 14. The analysis control unit 18 inputs the acquired time waveform of the detection signal to a display input unit 19, in addition to the information such as the phase input from the spectrum analyzers 13 and 14. Further, the analysis control unit 18 acquires a phase error between the spectrum analyzer 13 and the spectrum analyzer 14 based on the phase of the reference signal input from the spectrum analyzers 13 and 14. The phase error is information used when the time waveform of the detection signal described above is acquired. Details will be described below.

Further, the analysis control unit 18 is a control means that is electrically connected to the laser light source 2, the scan optical system 5, the spectrum analyzers 13 and 14, the signal synchronization unit 15, the pulse generator 17, and the signal switching switch 12, and controls these devices. Specifically, the analysis control unit 18 instructs the signal synchronization unit 15 to change the detection frequency.

The display input unit 19 displays information such as the phase and the amplitude acquired by the spectrum. analyzers 13 and 14, and information such as the time waveform of the detection signal acquired by the analysis control unit 18. Further, the display input unit 19 is a user interface, and receives input of the operational pulse signal, a desired detection frequency, or the like from the user.

Next, a flow of the measurement by the semiconductor device testing apparatus 1A will be described. In the measurement by the semiconductor device testing apparatus 1A, a process relating to acquisition of the phase error between the two spectrum analyzers 13 and 14 is first performed, and then a process of acquiring the time waveform of the detection signal input to the spectrum analyzer 13 is performed.

Figure 3:
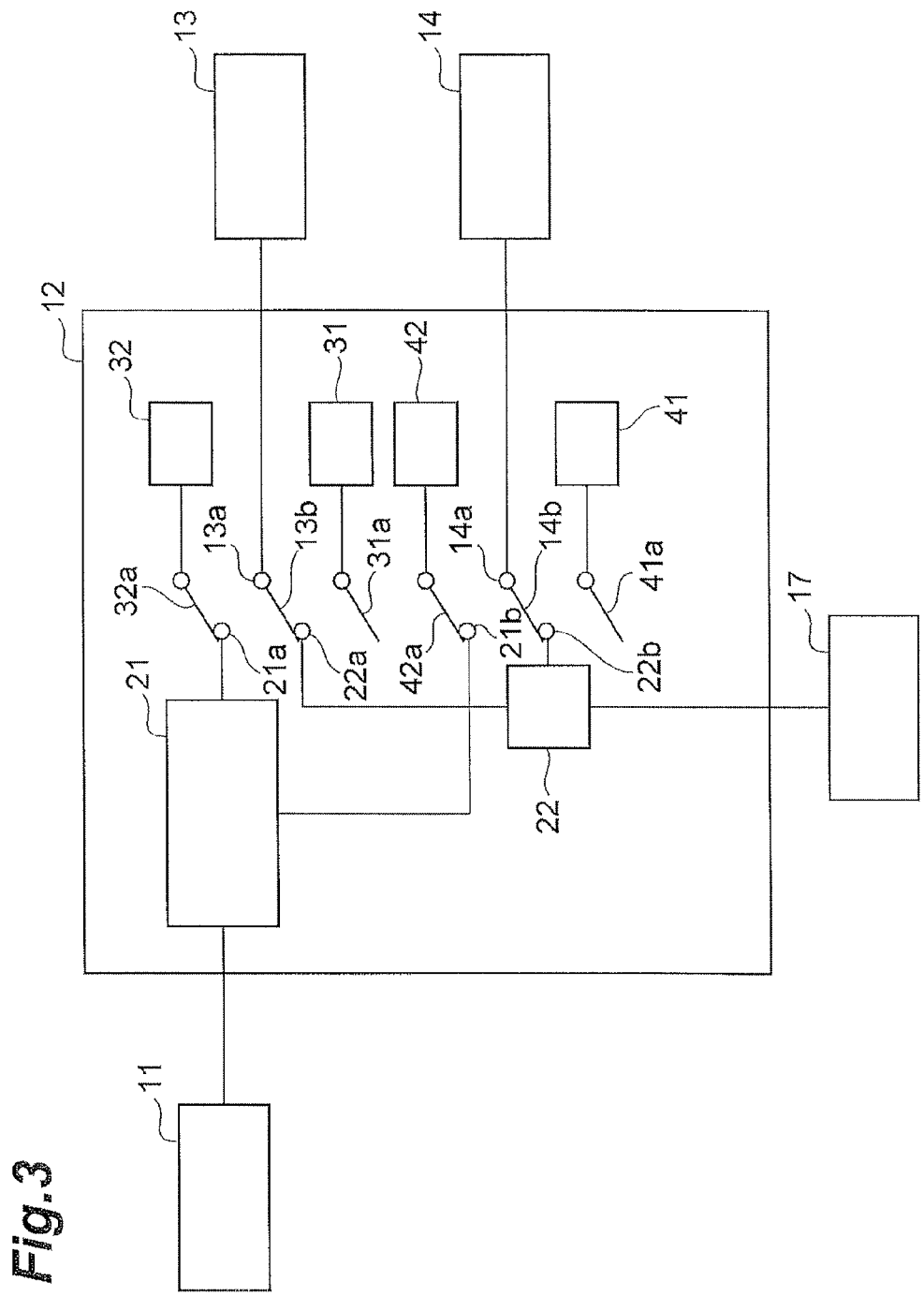
FIG. 3 is a diagram illustrating an example of a connection of the switch.
Figure 4:
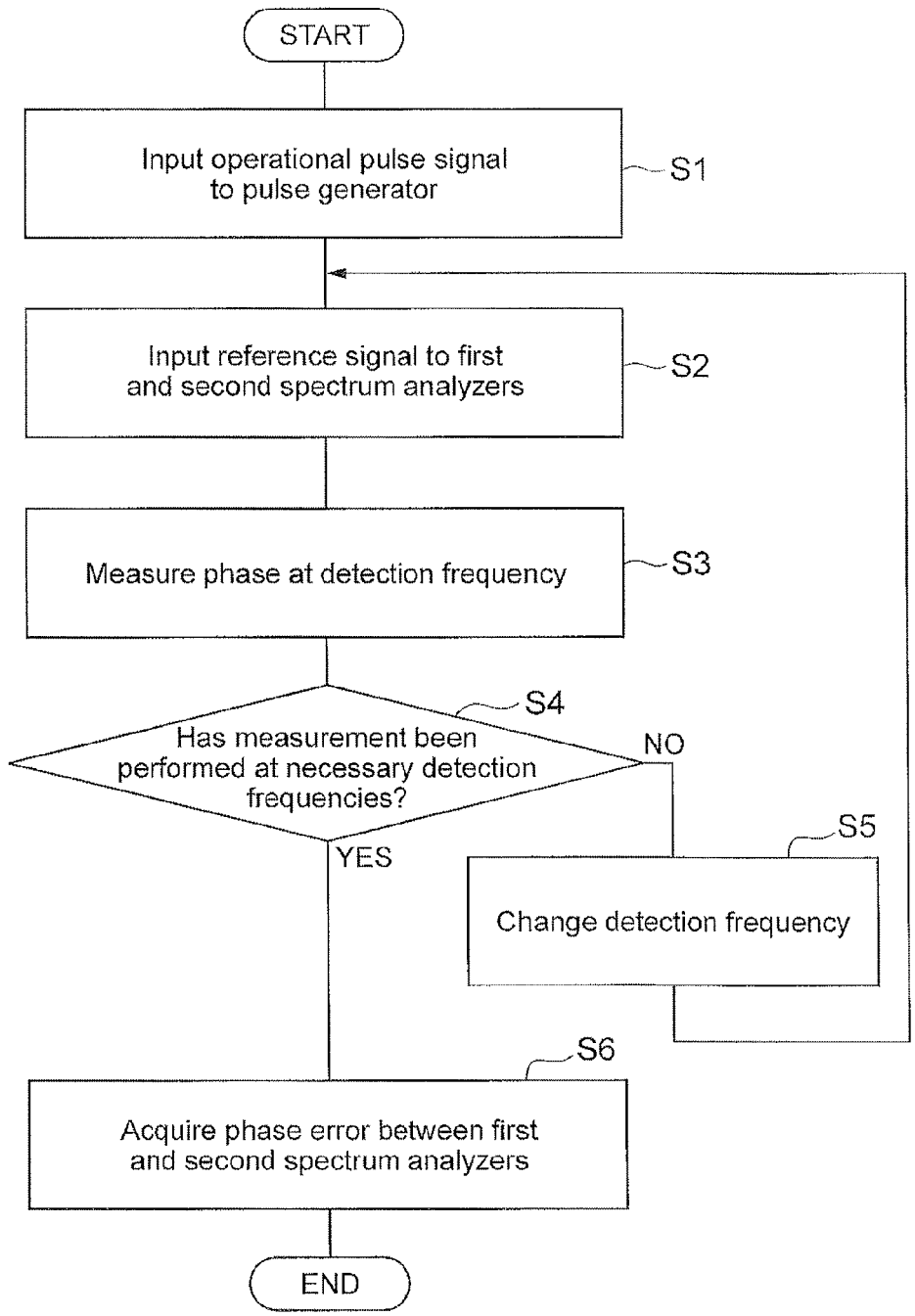
FIG. 4 is a flow diagram illustrating a phase error measurement process of the spectrum analyzer.

The process relating to acquisition of the phase error between the two spectrum analyzers 13 and 14 will be described with reference to FIGS. 3 and 4. When the phase error between the spectrum analyzers 13 and 14 is to be acquired, the reference signal generated by the pulse generator 17 is input to both of the spectrum analyzers 13 and 14. The signal switching switch 12 includes an isolation type signal branch 21 that branches the detection signal input by the amplifier 11, and a 50Ω branch 22 that branches the reference signal input by the pulse generator 17, as illustrated in FIG. 3. Further, the isolation type signal branch is a branch having a function for maintaining high isolation between outputs and between an input and an output, and is a branch including a combination of a directional combiner, an amplifier, and an attenuator. Further, the signal switching switch 12 includes a terminal 13a electrically connected with the spectrum analyzer 13, and a terminal 14a electrically connected with the spectrum analyzer 14. A connection portion 13b that can be connected to another terminal is connected to the terminal 13a, and a connection portion 14b that can be connected to another terminal is connected to the terminal 14a. Further, the signal switching switch 12 includes 50Ω terminators 31, 41, 32, and 42 that terminate the reference signal. A connection portion 31a that can be connected to another terminal is connected to the 50Ω terminator 31, a connection portion 41a that can be connected to another terminal is connected to the 50Ω terminator 41, a connection portion 32a that can be connected to another terminal is connected to the 50Ω terminator 32, and a connection portion 42a that can be connected to another terminal is connected to the 50Ω terminator 42. Also, a first terminal 21a that is one of branch destination terminals of the isolation type signal branch 21 can be connected to the connection portion 13b and the connection portion 32a, and a second terminal 21b which is the other terminal can be connected to the connection portion 14b and the connection portion 42a. Further, a first terminal 22a which is one of branch destination terminals of the 50Ω branch 22 can be connected to the connection portion 13b and the connection portion 31a, and a second terminal 22b which is the other terminal can be connected to the connection portion 14b and the connection portion 41a.

In the example illustrated in FIG. 3, the first terminal 22a of the 50Ω branch 22 that branches the reference signal is connected to the connection portion 13b, and the second terminal 22b of the 50Ω branch 22 is connected to the connection portion 14b. Further, the first terminal 21a and the second terminal 21b of the isolation type signal branch 21 are connected to the connection portion 32a of the 50Ω terminator 32 and the connection portion 42a of the 50Ω terminator 42, respectively. Accordingly, the reference signal is input to both of the spectrum analyzers 13 and 14.

Next, a specific process relating to the acquisition of the phase error between the spectrum analyzers 13 and 14 will be described. As a premise of the process, it is necessary for a connection situation of the signal switching switch 12 to be the same as that in the example illustrated in FIG. 3 described above. As illustrated in FIG. 4, first, the information on the operational pulse signal (for example, the operational pulse signal, a fundamental frequency or a fundamental period of the operational pulse signal, a reference clock of the pulse generator of the tester unit 16, or a frequency or a period of the reference clock) is input to the pulse generator 17 by the pulse generator of the tester unit 16 (step S1). Then, the reference signal synchronized with the operational pulse signal is generated and input to the signal switching switch 12 by the pulse generator 17. At this time, since the connection situation of the signal switching switch 12 is as illustrated in FIG. 3, the reference signal is input to the spectrum analyzers 13 and 14 (step S2).

Then, in each of the spectrum analyzers 13 and 14, the phase of the reference signal at a predetermined detection frequency is measured (step S3). Also, in the spectrum analyzers 13 and 14 (or the signal synchronization unit 15), it is determined whether measurement has been performed at all necessary detection frequencies set by the user in advance (step S4). When there is a detection frequency at which the measurement is not performed, the detection frequency is changed by the signal synchronization unit 15 (step S5), and the process of steps S2 to S4 described above is performed again. On the other hand, when the measurement is performed at all the necessary detection frequencies, the phase error between the spectrum analyzer 13 and the spectrum analyzer 14 is acquired based on a phase difference between the spectrum analyzers 13 and 14 at each detection frequency by the analysis control unit 18 (step S6). Further, it is preferable for the predetermined detection frequency to be a frequency of n times the repetition frequency of the operational pulse signal (n is a positive integer). In this case, it is possible to efficiently acquire the phase error. The phase error is information used when the time waveform of the detection signal is acquired. This is the specific process relating to the acquisition of the phase error between the spectrum analyzers 13 and 14.

Figure 5:
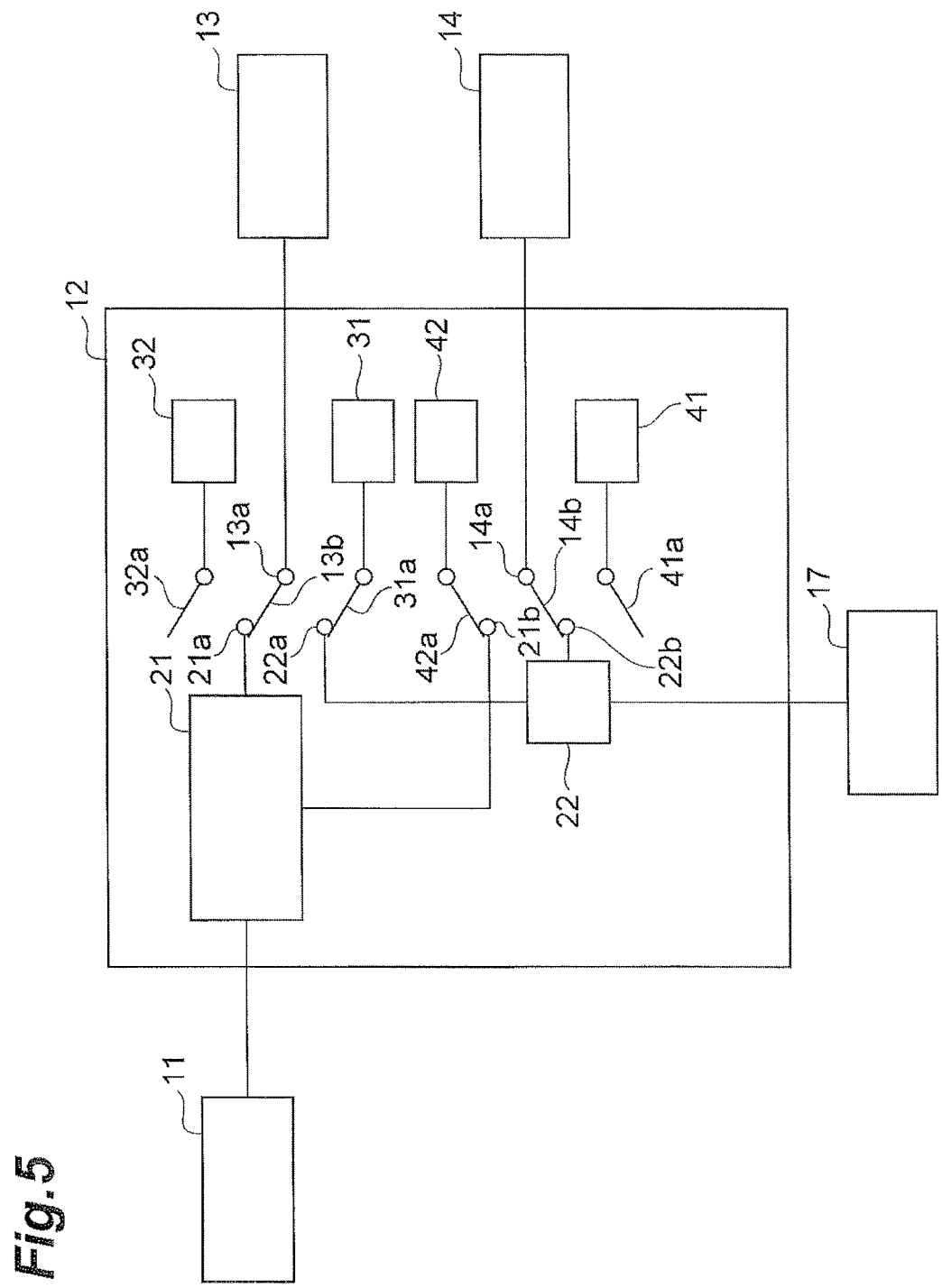
FIG. 5 is a diagram illustrating an example of a connection of the switch.

The process of acquiring the time waveform of the detection signal input to the spectrum analyzer 13 will be described with reference to FIGS. 5 and 6. When the time waveform of the detection signal is acquired, the detection signal is input to the spectrum analyzer 13, and the reference signal is input to the spectrum analyzer 14. In this case, in the signal switching switch 12, the first terminal 21a of the isolation type signal branch 21 that branches the detection signal is connected to the connection portion 13b, and the second terminal 22b of the 50Ω branch 22 is connected to the connection portion 14b, as illustrated in FIG. 5. Accordingly, the detection signal is input to the spectrum analyzer 13, and the reference signal is input to the spectrum analyzer 14. Further, in order to suppress generation of noise, the first terminal 22a of the 50Ω branch 22 is connected to the connection portion 31a of the 50Ω terminator 31, and the second terminal 21b of the isolation. type signal branch 21 is connected to the connection portion 42a of the 50Ω terminator 42.

Next, a specific process for acquisition of the time waveform of the detection signal input to the spectrum analyzer 13 will be described. As a premise of the process, it is necessary for the phase error between the spectrum analyzers 13 and 14 described above to have been acquired, and for the connection situation of the signal switching switch 12 to have been the same as that in the example illustrated in FIG. 5 described above.

Figure 6:
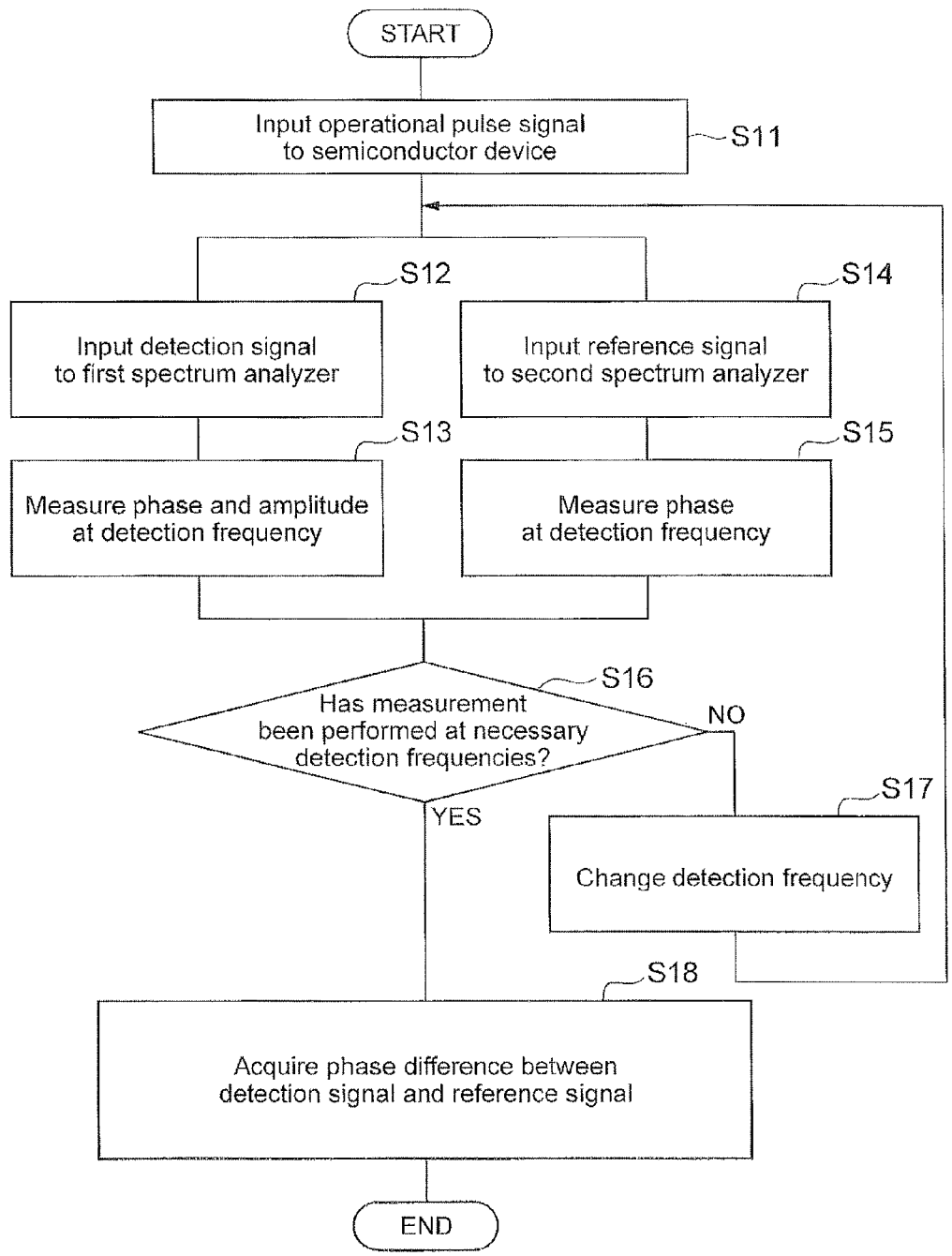
FIG. 6 is a flow diagram illustrating a process of acquiring a phase difference between a detection signal and a reference signal.

First, as illustrated in FIG. 6, the operational pulse signal is input to the semiconductor device 8 which is a measurement target by the pulse generator of the tester unit 16 (S11). The semiconductor device 8 is driven by the operational pulse signal. Further, the tester unit 16 inputs the information on the operational pulse signal (for example, the operational pulse signal, a fundamental frequency or a fundamental period of the operational pulse signal, a reference clock of the pulse generator of the tester unit 16, or a frequency or a period of the reference clock) to the pulse generator 17 at the same time as the input to the semiconductor device 8.

The detection signal is output as a response to the operational pulse signal input to the semiconductor device 8 by the optical sensor 10, and input to the spectrum analyzer 13 via the amplifier 11 and the signal switching switch 12 (step S12). In the spectrum analyzer 13, the phase and the amplitude of the detection signal at a predetermined detection frequency are measured (step S13).

On the other hand, in the pulse generator 17, the reference signal synchronized with the operational pulse signal is generated. The reference signal is input to the spectrum analyzer 14 via the signal switching switch 12 (step S14). In the spectrum analyzer 14, the phase of the reference signal at a predetermined detection frequency is measured (step S15).

When the process of steps S13 and S15 is completed, it is determined by the spectrum analyzers 13 and 14 (or the signal synchronization unit 15) whether a measurement has been performed at all necessary detection frequencies set by the user in advance (step S16). When there is a detection frequency at which the measurement has not been performed, the detection frequency is changed by the signal synchronization unit 15 (step S17) and the process of S12 to S16 described above is performed again. On the other hand, when the measurement is performed at all the necessary detection frequencies, a difference between the phase of the spectrum analyzer 13 and the phase of the spectrum analyzer 14 at each detection frequency is acquired by the analysis control unit 18, and a phase difference between the detection signal and the reference signal is acquired (step S18). Further, it is preferable for the detection frequency to be a frequency of n times the repetition frequency of the operational pulse signal (n is a positive integer).

Also, in the analysis control unit 18, the time waveform of the detection signal is acquired (reconfigured) through an inverse discrete Fourier transform based on the phase difference between the detection signal and the reference signal at each detection frequency, the amplitude of the detection signal at each detection frequency, and the phase error between the spectrum analyzers 13 and 14 described above. The acquired time waveform of the detection signal is displayed by the display input unit 19. This is the specific process for acquisition of the time waveform of the detection signal input to the spectrum analyzer 13.

As described above, in the semiconductor device testing apparatus 1A, the pulse generator 17 generates the reference signal containing the plurality of harmonics for the operational pulse signal input to the semiconductor device 8 in synchronization with the operational pulse signal. Also, the phase and the amplitude of the detection signal at the detection frequency are acquired by the spectrum analyzer 13, and the phase of the reference signal at the same detection frequency is acquired by the spectrum analyzer 14. Since the plurality of harmonics are contained in the reference signal, the phase difference between the detection signal and the reference signal in a high band, and the amplitude of the detection signal in the high band can be obtained when the detection frequency is a frequency in the high band. Accordingly, it is possible to acquire the time waveform of the detection signal in the high band, and perform the measurement of the detection signal at a high band frequency, which was difficult in the related art.

For example, a method of measuring a detection signal in a high band includes a measurement method using an oscilloscope in the related art. The oscilloscope measures signals in all bands at the same time. In this case, noise is a square root ($\sqrt{Hz}$) of a frequency band on the basis of a measurement band. Thus, for example, when a signal at 10 GHz is measured, noise of about 100000 times the noise when a signal at 1 Hz is measured is measured.

In this regard, in the semiconductor device testing apparatus 1A according to this embodiment, if the frequency serving as a measurement target is sufficiently stable, a measurement band of the signal is allowed to be very narrow, and noise can be correspondingly decreased. For example, when a signal at 100 MHz is measured and harmonics up to a $100^{th}$ harmonic (10 GHz) are measured, only noise at about 10 kHz is generated. Accordingly, the noise can be suppressed to be noise of about 100 times the noise when a signal at 1 Hz is measured. Thus, noise becomes $\frac{1}{1000}$ of the noise when the above oscilloscope is used, and an SN ratio of 1000 times can be realized. However, since harmonics up to a $100^{th}$ harmonic are measured in the semiconductor device testing apparatus 1A, measurement time of 100 times the measurement time of the oscilloscope simultaneously measuring signals in all bands is necessary. Therefore, when the measurement time is considered, in practice, an SN ratio of about 100 times the SN ratio when the oscilloscope is used is obtained. Further, a spectrum analyzer can generally be acquired at a much lower cost than an oscilloscope or a digitizer. Thus, according to the semiconductor device testing apparatus 1A, it is possible to perform the acquisition of the time waveform of the detection signal in the high band with a high SN ratio and at a low cost.

Further, the laser light source 2 that generates irradiation light that is the light radiated to the semiconductor device 8, and the scan optical system 5 that irradiates the semiconductor device 8 with the irradiation light and guides the reflected light are further included. The optical sensor 10 detects the reflected light to output the detection signal as a response to the operational pulse signal input to the semiconductor device 8. Accordingly, the acquisition of the detection signal as a response to the operational pulse signal is performed easily and reliably. Thus, it is possible to easily measure the detection signal in the high band and to increase measurement precision.

Further, the signal synchronization unit 15 functions as a changing unit that changes the detection frequency in synchronization with the reference signal. Specifically, the signal synchronization unit 15 changes the detection frequency of the spectrum analyzers 13 and 14 in C1 (FIG. 2) between the pulses of the pulse synchronization signal by synchronizing the spectrum analyzers 13 and 14 with the pulse generator (or the pulse generator 17) of the tester unit 16, thereby performing the measurement of the detection signal in a plurality of bands reliably and with high precision.

Further, the signal switching switch 12 that switches and inputs the detection signal and the reference signal so that the detection signal or the reference signal is input to the spectrum analyzer 13 is included. Accordingly, the reference signal can be input to both of the spectrum analyzer 13 and the spectrum analyzer 14, as necessary.

Further, the signal switching switch 12 performs switching so that the reference signal is input to the spectrum analyzer 13, the spectrum analyzers 13 and 14 acquire the phase of the reference signal at the detection frequency, and the analysis control unit 18 acquires a phase error between the spectrum analyzer 13 and the spectrum analyzer 14 based on the phase of the reference signal acquired by the spectrum analyzers 13 and 14. Accordingly, when the detection signal is input to the spectrum analyzer 13 later, the detection signal can be measured in consideration of the phase error between the spectrum analyzer 13 and the spectrum analyzer 14. Measurement precision of the detection signal in the high band is further improved.

Further, the pulse generator 17 can measure the detection signal at the high band frequency by generating the reference signal containing a primary harmonic (fundamental harmonic) to at least a tenth harmonic for the operational pulse signal.

Further, the pulse generator 17 can change the detection frequency between the pulses of the operational pulse signal by generating, as the reference signal, the pulse signal having a shorter pulse width than the operational pulse signal. Accordingly, it is possible to perform the measurement of the detection signal in a plurality of bands reliably and with high precision.

[Second Embodiment]

Next, a semiconductor device testing apparatus according to a second embodiment will be described in detail with reference to FIGS. 7 and 8. Further, differences with the above embodiment will be mainly described in description of this embodiment.

Figure 7:
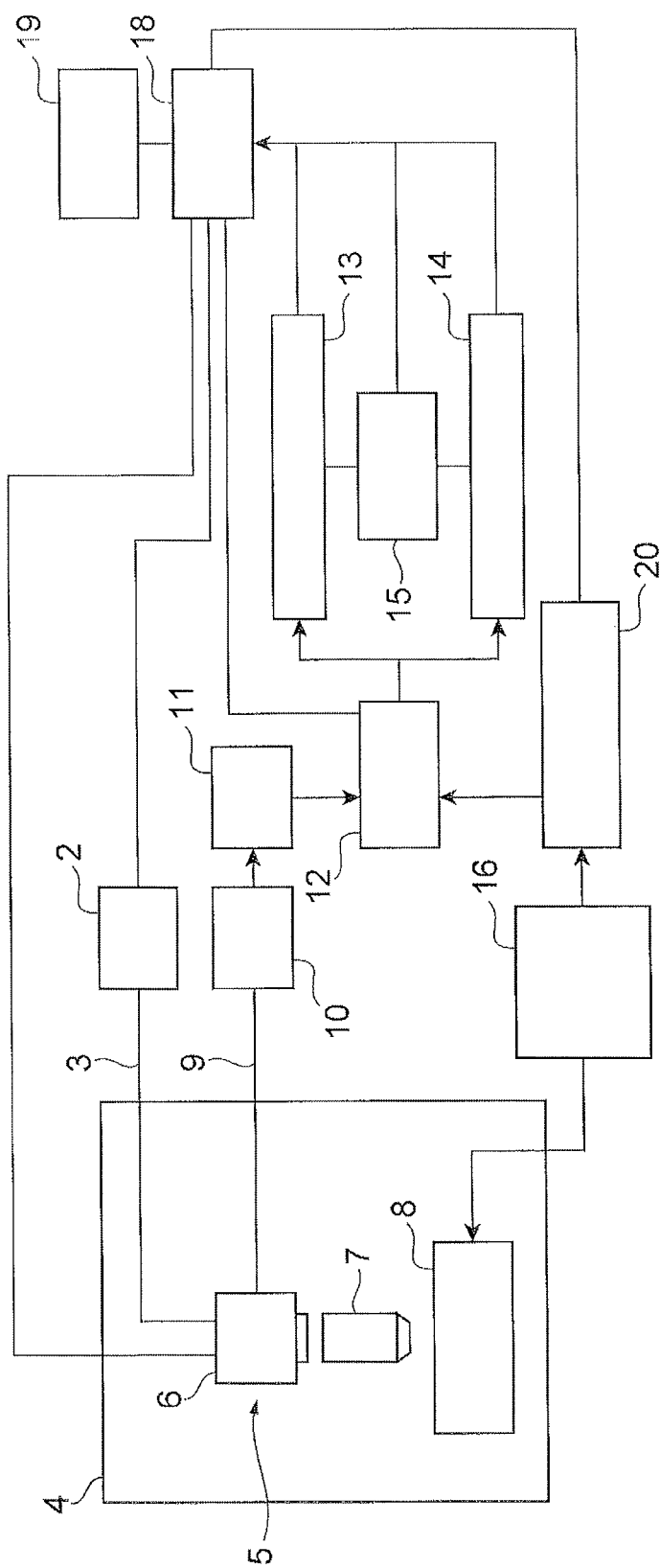
FIG. 7 is a diagram illustrating a configuration of a semiconductor device testing apparatus of a second embodiment of the present invention.

In a semiconductor device testing apparatus 1B according to this embodiment, a synthesizer 20 is used as a reference signal generation unit, as illustrated in FIG. 7. The synthesizer 20 continuously generates a sine wave having a different frequency synchronized to an operational pulse signal having a period T as a reference signal (see FIG. 8). That is, the synthesizer 20 continuously outputs sine waves synchronized to the operational pulse signal, as a sine wave corresponding to a fundamental wave of the operational pulse signal, a sine wave corresponding to a second harmonic, a sine wave corresponding to a third harmonic, . . . . A signal synchronization unit 15 changes detection frequencies of spectrum analyzers 13 and 14 to be the same frequency as the frequency of the sine wave corresponding to the $n^{th}$ harmonic output by the synthesizer 20. This change of the detection frequencies by the signal synchronization unit 15 is performed when the sine wave continuously output from the synthesizer 20 is switched.

Figure 8:
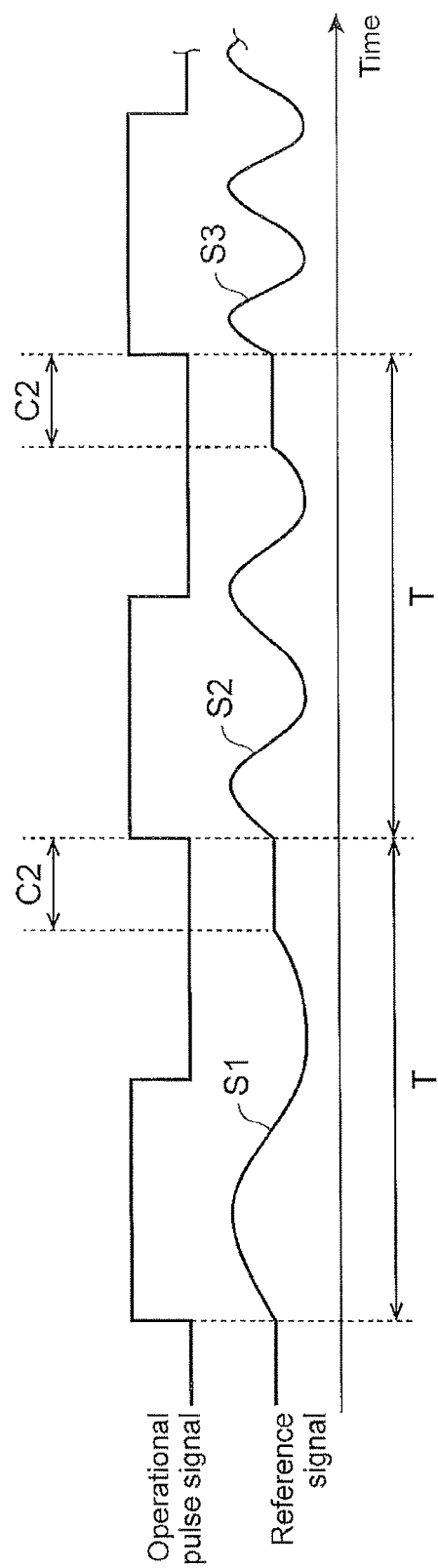
FIG. 8 is a graph illustrating an example of an operational pulse signal and a reference signal in the semiconductor device testing apparatus of FIG. 7.

In other words, the detection frequencies of the spectrum analyzers 13 and 14 are changed to the same frequency as that of a sine wave S2 by the signal synchronization unit 15 in a switching period C2 that is a period in which switching from a certain sine wave S1 to the next sine wave S2 occurs, as illustrated in FIG. 8. Further, the detection frequencies of the spectrum analyzers 13 and 14 are changed to the same frequency as that of a sine wave S3 by the signal synchronization unit 15 in a switching period C2 that is a period in which switching from a certain sine wave S2 to the next sine wave S3 occurs.

Thus, it is possible to perform the measurement of the detection signal in a plurality of bands reliably and with high precision by changing the detection frequencies of the spectrum analyzers 13 and 14 in the period in which the frequency of the sine wave is switched. Further, a cosine wave may be used in place of the sine wave corresponding to each harmonic. Further, a pulse generator that continuously generates, as the reference signal, a pulse signal having a different frequency synchronized with the operational pulse signal having a period of T may be used as the reference signal generation unit in place of the synthesizer 20.

While the embodiments of the present invention have been described above, the present invention is not limited to the above embodiments. For example, the light generation unit that generates light with which the semiconductor device 8 is irradiated is not limited to the laser light source 2, and may be a light source that generates coherent light other than the laser light, or may be a light source that generates non-coherent light using, for example, an SLD (super luminescent diode). In the light source using the SLD, since a semiconductor device is irradiated with the non-coherent light, it is possible to reduce interference noise. Further, heat may be applied to the semiconductor device 8 in place of an electrical signal.

Further, the first electrical measurement unit and the second electrical measurement unit are not limited to spectrum analyzers, and may be various electrical measurement devices such as a lock-in amplifier or an oscilloscope (or a device having functions thereof). Further, these electrical measurement devices may be combined. For example, the spectrum analyzer may be adopted as the first electrical measurement unit, and the lock-in amplifier may be adopted as the second electrical measurement unit. Further, a spectrum analyzer including a plurality of spectrum analysis units may be used.

Further, the frequency analysis apparatus according to the present invention is applicable to various devices for measuring a detection signal in a high band, as well as the semiconductor device testing apparatuses 1A and 1B. Further, while the frequency analysis apparatus according to the present invention shows effects in the measurement of the detection signal in the high band, the frequency analysis apparatus may be used in other bands, such as a low band.

What is claimed is:

1. An apparatus for frequency analyzing a measurement target, comprising:
   an operational signal generator configured to generate an operational pulse signal to be input to the measurement target;
   a detector configured to output a detection signal as a response to the operational pulse signal;
   a reference signal generator configured to generate a reference signal containing a plurality of harmonics for the operational pulse signal in synchronization with the operational pulse signal;
   a first electronic device configured to receive the detection signal and acquire a phase and amplitude of the detection signal at a detection frequency;

a second electronic device configured to receive the reference signal and acquire a phase of the reference signal at the detection frequency; and an analysis system configured to acquire a time waveform of the detection signal based on the phase and the amplitude of the detection signal and the phase of the reference signal.

2. The apparatus according to claim 1, further comprising:
a light source configured to generate light; and
an optical system configured to irradiate the measurement target with the light, and guide reflected light of the light,
wherein the detector is an optical sensor configured to output the detection signal by detecting the reflected light.

3. The apparatus according to claim 1, further comprising a changing device configured to change the detection frequency in synchronization with the reference signal.

4. The apparatus according to claim 1, further comprising a switching device configured to perform switching so that the detection signal or the reference signal is input to the first electronic device.

5. The apparatus according to claim 4,
wherein the switching device performs switching so that the reference signal is input to the first electronic device,
the first electronic device acquires the phase of the reference signal at the detection frequency, and
the analysis system acquires a phase error between the first electronic device and the second electronic device based on the phases of the reference signals acquired by the first electronic device and the second electronic device.

6. The apparatus according to claim 1,
wherein the reference signal generator generates the reference signal containing harmonics from a fundamental harmonic to at least a tenth harmonic for the operational pulse signal.

7. The apparatus according to claim 1, wherein the reference signal generator is a pulse generator, and generates, as the reference signal, a pulse signal having a shorter pulse width than a repetition period of the operational pulse signal.

8. The apparatus according to claim 1, wherein the reference signal generator continuously generates a signal at a different frequency as the reference signal.

9. The apparatus according to claim 1, wherein the first electronic device and the second electronic device are one or more spectrum analyzers.

10. A method of frequency analyzing a measurement target, comprising:

generating an operational pulse signal to be input to the measurement target;
outputting a detection signal as a response to the operational pulse signal;
generating a reference signal containing a plurality of harmonics for the operational pulse signal in synchronization with the operational pulse signal;
by a first electronic device, acquiring a phase and amplitude of the detection signal at a detection frequency based on the detection signal;
by a second electronic device, acquiring a phase of the reference signal at a detection frequency based on the reference signal; and
acquiring a time waveform of the detection signal based on the phase and the amplitude of the detection signal and the phase of the reference signal.

11. The method according to claim 10, further comprising generating light;
irradiating the measurement target with the light, and guiding reflected light of the light,
wherein the outputting step is outputting the detection signal by detecting the reflected light.

12. The method according to claim 10, further comprising changing the detection frequency in synchronization with the reference signal.

13. The method according to claim 10, further comprising switching so that the detection signal or the reference signal is input to the first electronic device.

14. The method according to claim 10, further comprising inputting the reference signal to the first electronic device,
by the first electronic device, acquiring the phase of the reference signal at the detection frequency, and
acquiring a phase error between the first electronic device and the second electronic device based on the phases of the reference signals acquired by the first electronic device and the second electronic device.

15. The method according to claim 10,
wherein the reference signal contains harmonics from a fundamental harmonic to at least a tenth harmonic for the operational pulse signal.

16. The method according to claim 10, wherein the reference signal is a pulse signal having a shorter pulse width than a repetition period of the operational pulse signal.

17. The method according to claim 10, wherein the reference signal is a pulse train having a plurality of pulses at a different frequency.

18. The method according to claim 10, wherein the first electronic device and the second electronic device are one or more spectrum analyzers.

* * * * *